United States Patent [19]

Carey et al.

[11] 4,440,497
[45] Apr. 3, 1984

[54] COMBINATION ABSORBANCE FLUORESCENCE ASPIRATING THERMAL CUVETTE

[75] Inventors: Glen A. Carey, North Ridgeville; Steven J. Hydo, Wellington, both of Ohio

[73] Assignee: Corning Glass Works, Corning, N.Y.

[21] Appl. No.: 378,598

[22] Filed: May 17, 1982

[51] Int. Cl.³ .............................................. G01N 1/10
[52] U.S. Cl. .................................... 356/246; 356/318
[58] Field of Search ................. 356/246, 339, 410, 73, 356/317, 318; 250/574, 576, 373

[56] References Cited

U.S. PATENT DOCUMENTS 3,515,491 10/1966 Emary .
3,646,313 4/1970 Gorgone-Emary .
4,088,407 5/1978 Schoeffel et al. ................ 356/246 X

OTHER PUBLICATIONS

Ashby et al., "A Variable Temperature Infra-Red Gas Cell Using Semiconductor Heat Pumps," *J. Sci. Instru.*, vol. 42, No. 5, pp. 326–327, May 1965.

Giggenbach, "A Simple Spectrophotometric Cell for Use with Aqueous Solutions up to 280° C.," *J. Phys. E.*, vol. 4, No. 2, pp. 148–149.

*Primary Examiner*—William L. Sikes
*Assistant Examiner*—Matthew W. Koren
*Attorney, Agent, or Firm*—B. R. Turner

[57] ABSTRACT

A flow cell is described comprising a solid liquid tight body having axial and radial optical paths. Absorbance and fluoroescence characteristics of a fluid sample in the cell may be measured simultaneously using the same exitation source. Means is provided for suppressing bubble formation and turbulence. Flow cell temperature is controlled using a solid state heat pump.

9 Claims, 6 Drawing Figures

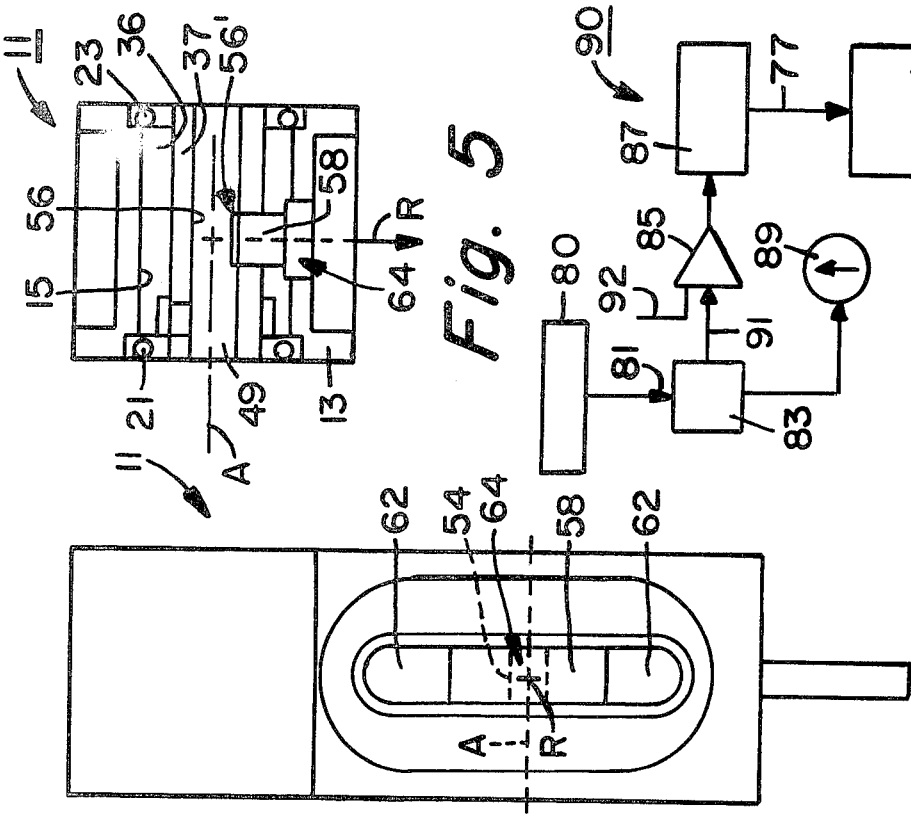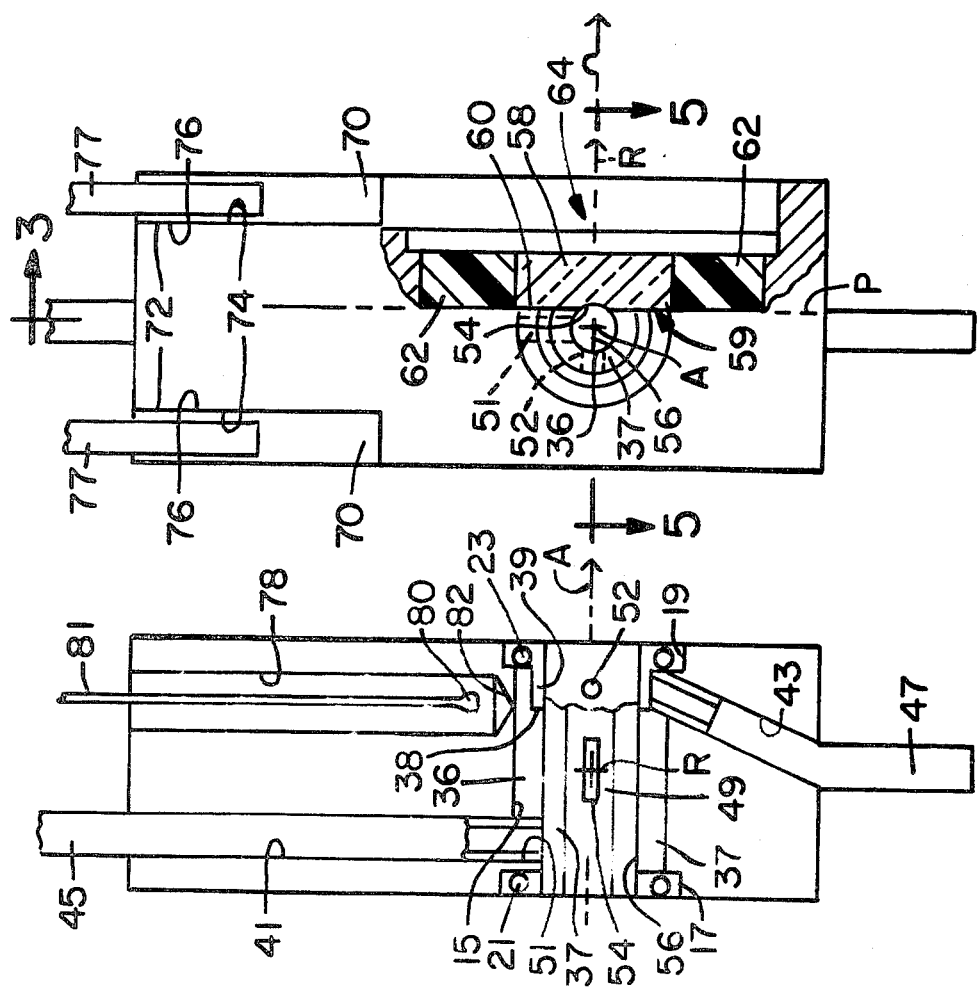

COMBINATION ABSORBANCE FLUORESCENCE ASPIRATING THERMAL CUVETTE

BACKGROUND OF THE INVENTION

This invention relates to flow cells for receiving successive fluid samples to be examined by a plurality of radiant energy measuring devices. In particular, the invention relates to a novel flow cell unit or cuvette having an especially configured bore and insertable sample receiving chamber for use with a micro-sample spectrometer or fluorometer or similar measuring device. The chamber has an axial through window and a transverse side window. The interior of the bore has smooth viewing surfaces such that optical density and fluorescence characteristics of the sample in the chamber can be accurately ascertained.

Presently, there are two conventional methods for determining optical characteristics of a plurality of small fluid samples. One such method is to place each sample in a separate container, test tube or cuvette and position the container in the flow path of a beam of light or other radiant energy provided by a spectrophotometer or flourometer. Such method is subject to uncontrollable error due to physical variations between sample containers which cause differences in optical characteristics.

The other conventional method and that employed by the fluid sample flow embodied herein involves the use of a single sampling container as set forth in U.S. Pat. Nos. 3,515,491 and 3,646,313. Unfortunately, the use of a single container is attended by its own problems including the formation of bubbles which lie in the optical path and the inability to easily detect different optical characteristics.

The improved flow cell of this invention all but obviates the above problems by the use of simplified bubble prevention techniques and a multi-purpose viewing system.

SUMMARY OF THE INVENTION

The subject flow cell comprises a solid body having a cylindrical bore passing therethrough. Each end of the bore has a demountable liquid-tight sealing means as well as demountable means forming a narrow axial optical path for the entrance and exit of a beam of light for use by an instrument such as a micro-spectrophotometer. Adjacent both ends of the bore and generally perpendicular to its axis are fluid entrance and exit ports communicating to the exterior of the cell body. The exit port has its interior end opening into an annular well of a diameter larger than and coaxial with the bore. The exterior end of the exit port is connected to a source of vacuum. The exterior end of the entrance port is to be connected to a source of a test sample. A cylindrical sample receiving and containing insert is receivable into the bore. The insert has an axial cylindrical bore and radially formed fluid entrance and exit passageways which abut the entrance port and annular well respectively. The body of the flow cell has a lateral opening therein intermediate the entrance port and annular well. The insert has a radial side window opening in communication with the axial cylindrical opening therein and the lateral opening in the cell body. A window element is fitted into the side window opening of the insert. An optical face of the window adjacent the interior of the inset is formed so as to conform to the cylindrical shape of the axial bore therein. The interior surface of the cylindrical bore in the insert is smooth and the formation of turbulent flow of fluid samples therethrough is thereby prevented. A separate insert sleeve may be provided between the cylindrical opening within the body and the insert for centering and securing the same in the body.

DESCRIPTION OF THE DRAWINGS

FIG. 2 is a partially fragmented end view of the flow cell of the present invention.

FIG. 3 is a vertical section taken along line 3—3 of FIG. 2.

FIG. 4 is a side view of the flow cell showing a detail of a side window.

FIG. 5 is a section taken along 5—5 of FIG. 2.

FIG. 6 is a schematic diagram in block form showing an electrical control circuit for governing the temperature of the flow cell of the present invention.

Figure 1:
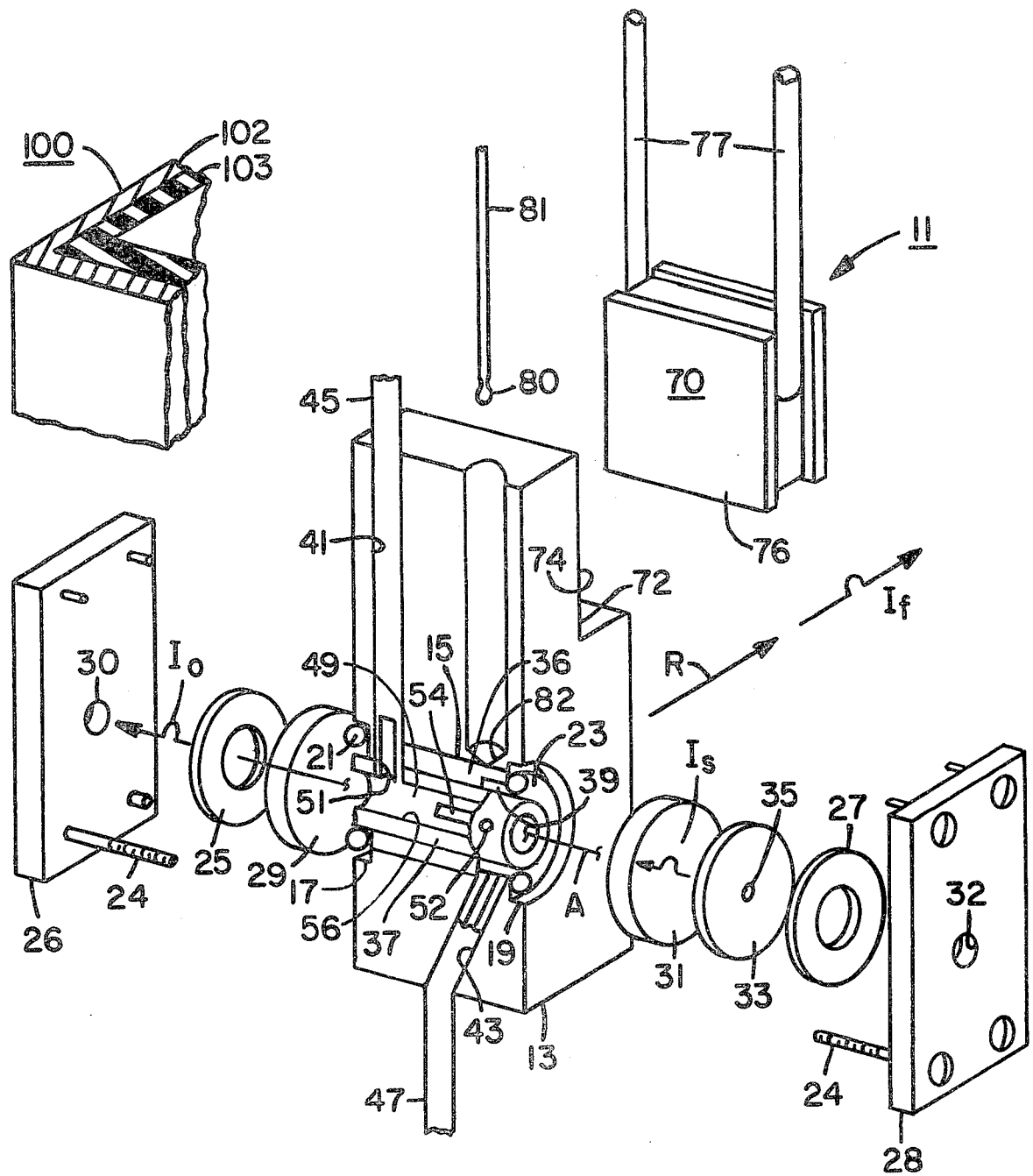
FIG. 1 is a partially exploded and fragmented perspective view of the flow cell taken along a vertical section.

It will be appreciated that, in the following description and in the drawings, certain portions thereof may be magnified for clarity.

DESCRIPTION OF THE PREFERRED EMBODIMENTS

With reference to FIGS. 1-5 and particularly FIG. 1 there is shown a fluid flow cell 11 having a body 13. The body contains a cylindrical bore 15 having a pair of annular seats 17 and 19 for receiving O-rings 21 and 23. Glass plates or windows 29 and 31 seat against respective O-rings 21 and 23. An opaque cover 33 having a central pinhole 35 mounts over the glass 31.

Prior to assembly of the above identified parts, an annular sleeve 36 may be positioned in bore 15. A hollow sample retaining insert 37 may be positioned in the sleeve 36. The assembly is completed as shown in FIG. 1. Washer springs 25 and 27 may be used to bias the respective glass plates 29 and 31 against the O-rings 21 and 23. Opposed face plates 26 and 28 having respective openings 30 and 32 are secured together by long screws 24 for urging the springs 25 and 27 against the glass plates 29 and 31 for sealing the body 13. In this manner the ends of the bore 15 and the hollow chamber of insert 37 are sealed against liquid loss. There is defined by the foregoing an unobstructed optical path A passing through the pinhole 35 and axially through the insert 37 and terminating exterior of the window 29. The windows 29 and 31 are parallel to each other and are perpendicular to optical path A.

It is desirable that the pinhole 35 be as small as possible so as to columnate the beam of light passing through the cell. However, the size of the pinhole 35 is also determined by the sensitivity of the test instrument, the length of the optical path, and the intensity of the light source. The entire flow cell 11 is designed to prevent stray light entering the optical path.

Attention is directed to FIGS. 1, 3 and 5 which show details of the sleeves 36 and insert 37 in body 13. Near one end of insert 37 there is provided an entrance port 41. Near the opposite end of the bore 15 and generally obliquely offset to the entrance port 41 is an exit port 43. Respective hollow inlet and outlet tubes 45 and 47 are received by the entrance and exit ports 41 and 43, as shown. The inlet tube 45 is to be coupled, via conduits not shown, to a source of a fluid sample, also not shown.

The outlet tube 47 is to be coupled to vacuum means, not shown, for drawing or aspirating the fluid sample therein. An annular well 39 is formed as a counterbore in sleeve 36. The annular well has a diameter greater than insert 37 and is located in communication with the exit port 43.

It will be seen that the insert 37 is preferably of right circular cylindrical form and has a central coaxial fluid chamber or passageway 49 therethrough. Near one end of the insert 37, the entrance end, there is provided a radially bored entrance hole 51. The entrance hole 51 receives inlet tube 45 and when the insert 39 is positioned as in FIGS. 1 and 2, the hole 51 provides direct communication between the passageway 49 and the inlet tube 45 via the entrance port 41.

Near the opposite end of the insert 37 there is provided an exit hole 52 offset 90° from the entrance hole 51. The exit hole 52 couples the fluid passageway 49 with annular well 39 and outlet tube 47 via exit port 43. Exit hole 52 is preferably horizontally disposed when in use as shown in FIG. 2. The combination of the exit hole 52 and annular well 39 helps to reduce turbulence and bubble formation in a manner similar to that described in the U.S. Pat. No. 3,515,491 referred to above. The design of the insert 37 of the present invention is simplified requiring only offset respective inlet and outlet holes 51 and 52.

Referring now to FIGS. 1-5, the insert 37 has an ., axially aligned aperture or slit 54 located therein. The slit 54 is formed by a plane notch 59 in an exterior portion of the right circular cylinder forming the insert 37. The notch 59 lies in a plane P parallel to the optical path A (sometimes herinafter axis A) of the insert 37.

A portion of an inside surface; or sidewall 56 of the passageway 49 is removed by the notch 59 providing a radial optical path R from the interior of the fluid passageway 49 radially from axis A out of the slot 54 (see FIG. 2.)

A transparent cover 58 preferably manufactured of fused quartz is located against a flat surface portion 60 of the notch 59. The cover 58 closes the fluid passageway 49 forming a side window 64 along the radial optical path R from the interior of the passageway 49. A sealing compound 62, such as a two-part thixotropic epoxy resin manufactured by TRA-CON Inc. and designated TRA-BOND 2126, may be used to secure the quartz forming the window 64 against the flat surface 60 of notch 59 to thereby seal the side window 64 against leaks. An interior surface 54 of the glass or quartz cover 58 forming the side window 64 is ground in a cylindrical shape, as shown, conforming to the shape of the interior surface 56 of fluid passageway 49. The cover 58 and insert 37 are formed such that the interior of the fluid passageway 49 has smooth walls. Thus, the possibility of turbulent flow and bubble formation in the passageway 49 is effectively eliminated.

The present invention also includes an improved means for controlling the temperature of body 13, the insert 37 and a sample fluid flowing therethrough. There is provided a pair of thermo-electric devices 70 such as model No. 110-4 manufactured by Borg Warner Corporation (see FIGS. 1 and 2). The thermo-electric devices 70 are preferably connected and operate as solid state heat pumps. That is, they may provide active heating and cooling in reversible directions depending upon a control current. The body 13 of the flow cell 11 is fabricated from a highly conductive material such as aluminum and the sleeve 36 and insert 37 are manufactured from conductive metal such as stainless steel. The body 13 has a pair of recesses 72 for receiving the thermo-electric devices 70 in close abutting relationship. Vertical surfaces 74 of the body 13 are in intimate contact with an operative face 76 of each of the thermoelectric devices 70. A thermally conductive grease or epoxy, not shown, may be applied to face 76 and surface 74 to secure each thermo-electric device 70 in good thermal conducting relationship with the body 13.

In order to control the temperature of the fluid sample; in passageway 49 a thermal sensing device is required. In FIGS. 1 and 2, there is shown a vertical hole 78 formed: within the body 13 and a thermistor 80 located therein. The thermistor 80 may be secured in good thermal contact with sidewalls of the hole 78 by means of a thermally conductive grease or other material, not shown. The thermister 80 extends down towards bottom end 82 of the hole 78 in close proximity to the insert 37. The position of the temperature sensing thermistor 80 causes it to be especially responsive to the temperature of the fluid sample while not being adversely influenced by the temperature of other portions of the body 13.

The thermistor 80 is coupled by exterior leads 81 to a control circuit 90 shown in FIG. 6. The control circuit 90 includes an electrical bridge 83 having one arm that contains the thermister 80. The balancing arm of the bridge 83 opposite the thermistor 80 contains calibrated precision resistors (not shown) matching the characteristics of the thermistor 80 at selected control point temperatures. The balance of the bridge 83 is applied over line 91 to an operational amplifier 85 which drives a power applying means 87 such as a series connected transistor which in turn is connected by leads 77 to the thermo-electric devices 70. A null meter 89 monitors the resistances of the thermister 80 and the precision resistors to provide operational control. Initial deviations from null balance can be corrected by human operator readjustment or if desired automatic control means not shown to alter power through the thermoelectric device 70 to bring the system into null balance. Such readjustments can be applied to the amplifier 85 as a bias signal for summing therein over lead 92.

In operation, the bridge 83 is preset to be balanced at a precise temperature of fluid sample in passageway or chamber 49. The thermistor 80 reports the sample temperature to the bridge 83 as a function of deviation or imbalance caused by a change in the amount of power applied to the thermo-electric devices 70 to thereby remove the inbalance. Balancing current to the thermoelectric devices 70 may be supplied in one polarity to cause the thermo-electric devices 70 to provide cooling to the body 13 of the flow cell 11. Similarly, reverse current can be used to operate the thermoelectric devices 70 in a heating mode if necessary. The high thermal conductivity of the insert 37 and the body 13 combined with the sensing position of the thermistor 80 enable the invention to maintain sample temperature to within better than 0.2 degree of the control point. Hence, temperature changes are precisely monitored and controlled very accurately. The above arrangement is similar to that described in U.S. Pat. No. 3,646,313 except, however, that thermo-electric devices 70 provide both heating and cooling for the flow cell 11. Other arrangements for controlling the temperature of the flow cell 11 may be provided by various electrical circuits for driving the thermo-electric devices 70. The control system 90 described and shown in FIG. 6 is one of many possible variations for such control.

In operation, the present invention has a dual mode. First, a source of light (not shown) provides radiant energy which is collimated by the cover 33 and pinhole 35 as source energy $I_s$. The collimated energy thus produced passes through the window 31 along the optical path A through the fluid and out of the window 29. A portion of the source energy $I_s$ having been absorbed by the fluid reduces the radiant light energy exiting the window 29 to some output energy $I_o$. This energy may be detected by a spectrophotometer (not shown) to provide an indication of the absorbance of the fluid passing through the cell 11.

Concurrently with the absorption measurement herein described, fluorescence measurement may be obtained. If the fluid is a fluorescent material it will absorb some of the source energy $I_s$ and release photons at a different wavelength. Some of the photons produced will escape through the radial optical path R as hereinbefore described and form a beam of such fluorescent energy $I_f$ exiting through the slit 54 and side window 64. (See FIGS. 1 and 2). This energy may be detected by a fluorometer (not shown) which will provide a level measurement of the fluorescence of the fluid sample. Thus, absorbance and fluorescence of a material may be measured simultaneously using a single energy source and a plurality of detectors each independently reading an energy level desired. It should be noted that there may be a fluorescence error introduced into the absorbance measurement and vice versa. However, there are known techniques for making corrections for such errors and the present invention provides sufficient information to make such corrections. (See: Fluorescence Assay; Odenfriend, 1962, Academic Press, pages 108 and 109).

Although not detailed herein, except schematically in FIG. 1, a suitably apertured external housing 100 may be provided for supporting the flow cell 11 of the present invention in a manner similar to that described in the U.S. patents hereinbefore noted. Such external housing 100 may include an insulating layer or jacket 101 and an external metallic cover 102. The insulating jacket 101 isolates the flow cell 11 from ambience and the cover 102 supports the entire assembly in an instrument or the like. A wide variety of choices for the insulating jacket 101 and cover 102 are available depending on the instrument interface.

While there has been described what at present is considered to be the preferred embodiment of the present invention, it will be obvious to those in the art that various changes and modifications may be made therein without departing from the invention and it is intended in the appended claims to cover all changes and modifications as fall within the true spirit and scope of the invention.

What is claimed is:

1. An aspirating abosrbance thermal flow cell or cuvette for containing therein a fluid sample to be tested under the influence of an external light source comprising:

a housing having a chamber therein formed with a cylindrical sidewall, said chamber having an inlet and outlet for communicating the fluid sample along a flow path through the same from the inlet to the outlet, the chamber having spaced apart opposed openings centered along a straight line axial optical path and a notch opening in the sidewall, intermediate the opposed openings, forming an axial slot therein;

a pair of first transparent optical windows in the form of flat sided circular disks, one located in each of the opposed openings and being oriented with the flat sides perpendicular to the optical path, the disks closing the opposed openings in the chamber and providing a through window into and out of the chamber for passage of light from the external source through the fluid sample, the light being attenuated in intensity as it passes through the fluid sample, the attenuation being a function of an absorbance characteristic of the fluid sample; and a second transparent optical window, sealed within the slot for closing the side opening and providing a radial optical path for passage of fluorescent light from within the chamber to without the same, said fluorescent light being a function of a fluorescence characteristic of the fluid resulting from exitation by the light from the external source.

2. A flow cell as defined in claim 1 wherein the first and second optical windows have surface portions in communication with fluid sample and said surface portions do not substantially protrude within the flow path thereby reducing the introduction of turbulence in the fluid sample flow path.

3. A flow cell as defined in claim 1 further including: heat pump means in thermal communication with the chamber for adding heat thereto and drawing heat therefrom in accordance with the state of said heat pump means; a temperature detector in communication with the chamber for detecting the temperature thereof and; control means including a set point means for establishing a desired temperature of the flow cell, said control means responsive to the temperature detector and a set point and coupled to the heat pump means for controlling the state thereof in accordance with the sensed temperature and the set point.

4. A flow cell as defined in claim 1 wherein the second transparent optical window has a face proximate the interior of the cylindrical sidewall of the chamber and said face is formed with a surface lying within a surface formed of the interior of the cylindrical sidewall such that the second transparent optical window does not protrude within the chamber nor is it recessed therefrom.

5. A flow cell as defined in claim 1 wherein the housing has relatively high thermal conductivity and further including: temperature control means for precisely maintaining the temperature of the fluid sample within the chamber by reversible application of heating and cooling.

6. A flow cell as defined in claim 5 wherein the temperature control means comprises: thermo-electric heating and cooling means mounted in thermal contact with said housing, yet relatively remote from said chamber; electrical temperature sensing means mounted within said housing and positioned close to the chamber and relatively remote from the heating and cooling means so as to be primarily responsive to the temperature of the fluid sample in the chamber rather than the heating and cooling means; and means for comparing the temperature measured by the sensing means with a selected set point value and applying power to said heating and cooling means in proportion to an output of said means for comparing.

7. A flow cell as defined in claim 6 in which temperature control means comprises: electrical bridge means connected to be balanced at the set point value and to be unbalanced, upon receipt from said electrical temperature sensing means, a sample fluid temperature signal different from the set point value.

8. A flow cell as defined in claim 7 in which said control means further comprises: electrical power applying means coupled between said bridge means and said heating and cooling means, and bridge balance monitoring means coupled to said bridge means for surveillance of the operation of the temperature control of said electrical components.

9. A flow cell as defined in claim 8 further comprising: insulating means for receiving the housing of the flow cell therein for isolating the same from ambience, and an external jacket surrounding said insulating means.

* * * * *